United States Patent [19]

Sklar

[11] 4,043,754
[45] Aug. 23, 1977

[54] INSTRUMENT STERILIZING PIN

[75] Inventor: Alan L. Sklar, Hewlett Harbor, N.Y.

[73] Assignee: J. Sklar Mfg. Co., Inc., Long Island City, N.Y.

[21] Appl. No.: 700,543

[22] Filed: June 28, 1976

Related U.S. Application Data

[63] Continuation of Ser. No. 528,982, Dec. 2, 1974, abandoned.

[51] Int. Cl.² .......................... A61L 3/00; A61L 3/02
[52] U.S. Cl. ...................................... 21/82 R; 21/83; 21/105; 24/85 C; 150 B/; 211/60 T; 248/220.4
[58] Field of Search ............. 16/114 R; 248/317, 340, 248/223, 224, DIG. 3; 99/403, 450; 21/83, 103, 105, 82 R, 82 H; 24/150 B, 85 C, 73 R, 213 R, 153 US, 224 W, 261 A, 261 FY; 211/60 T, 184; 224/46 T, 48 R

[56] References Cited

U.S. PATENT DOCUMENTS

| | | | |
|---|---|---|---|
| 801,756 | 10/1905 | Wemple | 21/105 |
| 1,267,322 | 5/1918 | Holles | 21/83 |
| 1,554,527 | 9/1925 | Saalfrank | 24/150 B |
| 2,108,950 | 2/1938 | Stober | 24/261 A |
| 2,952,343 | 9/1960 | Modrey | 248/DIG. 3 |
| 2,963,164 | 12/1960 | Watson | 248/DIG. 3 |
| 3,091,423 | 5/1963 | Butterworth | 211/60 T |
| 3,305,102 | 2/1967 | Saphirstein | 211/184 |
| 3,427,084 | 2/1969 | Sinclair | 211/184 |

Primary Examiner—Barry S. Richman
Attorney, Agent, or Firm—Amster & Rothstein

[57] ABSTRACT

This invention relates to a combination of a substantially U-shaped pin and sterilizing tray arrangement for holding surgical instruments during sterilization. The tray has a bottom surface made of perforated metal and the U-shaped pin has two substantially parallel legs including engaging segments adapted to be inserted into correspondingly spaced holes in the perforated metal bottom surface of the tray. Surgical instruments are positoned within the tray with the sterilizing pins keeping the instruments in the most advantageous position for proper sterilization.

1 Claim, 6 Drawing Figures

U.S. Patent    Aug. 23, 1977    4,043,754
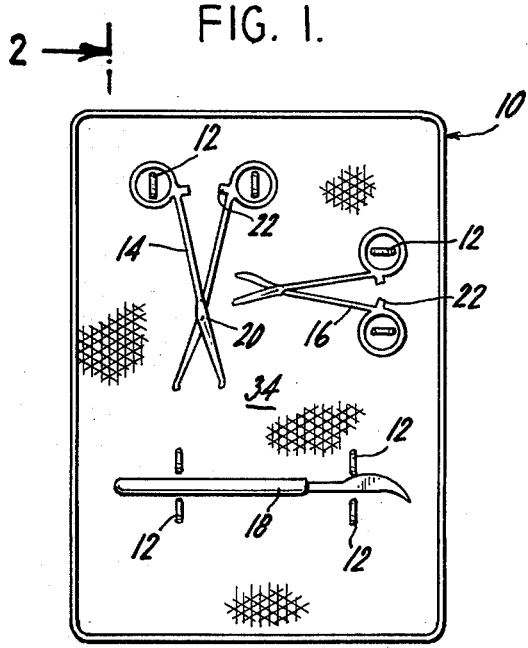
FIG. 1.
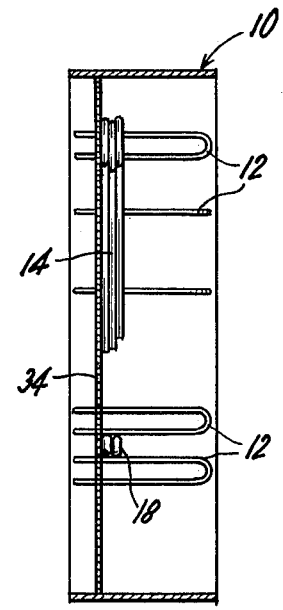
FIG. 2.
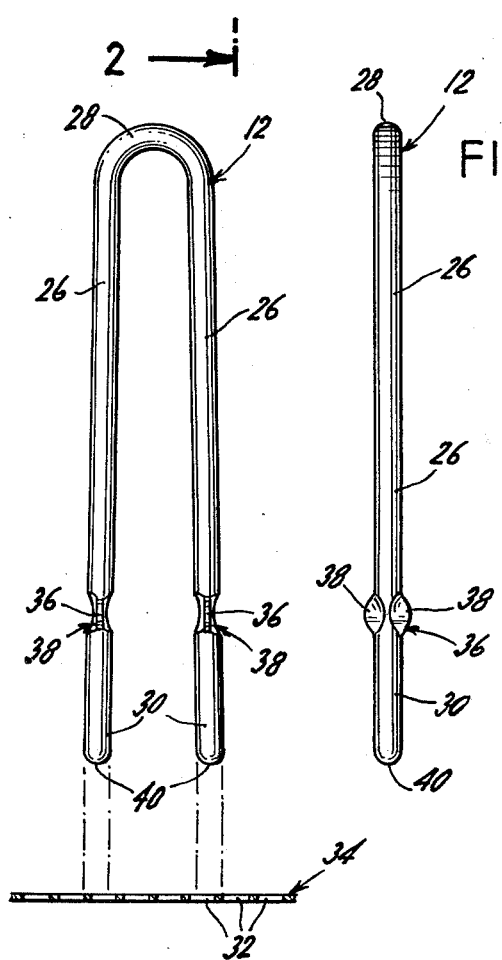
FIG. 3.
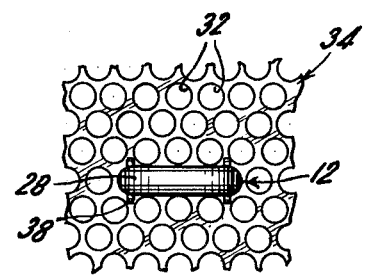
FIG. 4.
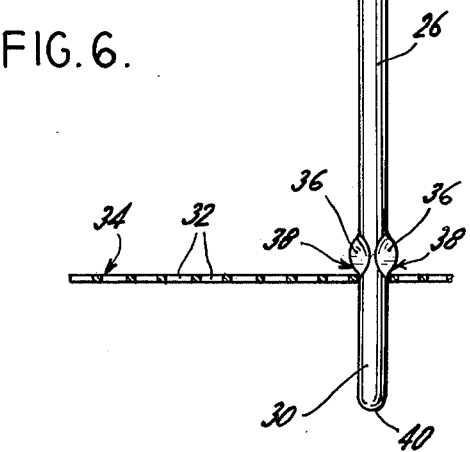
FIG. 5.
FIG. 6.

INSTRUMENT STERILIZING PIN

This is a continuation of application Ser. No. 528,982 filed Dec. 2, 1974, now abandoned.

This invention relates to a surgical instrument or sterilizing arrangement including an instrument retaining pin adapted to be used in conjunction with a sterilizing tray.

Prior to this invention, surgical instruments having ring handles, such as scissors, clamps and some types of forceps, have been sterilized in trays by placing one of the conventional types of sterilizing racks through the finger rings in the surgical instrument handles. A typical sterilizing rack is comprised of a pair of corresponding U-shaped pieces of such configuration that the parallel legs of the U-shaped pieces are spaced from each other a distance approximately equal to the distance between the finger rings of the instrument. The sterilizing racks are loaded by inserting the parallel legs of one U-shaped piece through the finger rings of the surgical instrument. After a sufficient number of instruments are placed on the U-shaped piece, the rack is engaged with a second corresponding U-shaped piece captivating the instruments to be sterilized. The assembly is then loaded in a sterilizing tray for sterilization. The assembly of instruments on these racks is necessarily time-consuming — and, due to the varying size and nature of the surgical instruments loaded on the rack, some instruments on the rack will be in their open position while others are closed.

Another type of conventional sterilizing rack is similar in appearance to a safety pin. Such a rack is utilized by passing its end through one ring of the handle of a surgical instrument.

The principal object of the present invention is to provide a means whereby surgical instruments can be more conveniently loaded in a sterilizing tray, obviating the necessity of threading a rack through the handle of the instrument.

It is another object of this invention to provide a means whereby surgical instruments of the same general size or configuration can be sterilized together in such manner that all similar instruments are in a corresponding position allowing maximum exposure of the surfaces in the instrument for more complete sterilization.

It is a further object of this invention to provide a surgical instrucment holder that may be used for positioning ring handled as well as other types of surgical instruments in a sterilizing tray.

It is a still furthe object of this invention to provide a convenient method of stacking and separating instruments in the sterilizing trays, thus avoiding the necessity of a separate sorting operation.

Finally, it is an object of this invention to provide a means whereby the handling of surgical instruments after sterilization is minimized because the instruments can be maintained in the presorted arrangement without reducing the effectiveness of the sterilization process.

In accordance with an illustrative embodiment demonstrating objects and features of the present invention, there is provided an instrument sterilizing pin having two legs adapted to engage the perforations in the bottom surface of a sterilizing tray. The sterilizing pin preferably includes stop means on its legs such that when the legs are inserted into the perforated bottom surface of the tray, a positive stop is provided when the clip is fully inserted.

The spacing between the bottom ends of the legs is slightly larger than the spacing between the corresponding holes in the perforated metal bottom surface of the tray requiring a deflection of the leg segments incident to the insertion of the pins. The pins are of a resilient material so that deflection causes the pin to be in a tensed condition after insertion, with the restoring force of the pin legs assuring that the sterilizing pin will remain engaged in the sterilization tray during sterilization and the handling incident thereto.

Prior to the sterilizing process several sterilizing pins are inserted in the perforated metal bottom surface of a sterilizing tray. Ring-handled surgical instruments are then placed in the tray with the ring handles around the sterilizing pins oriented within the tray such that the instruments can be arranged to lie in their open position, maximizing the exposure of various instrument parts such as box locks and ratches during sterilization.

The above description as well as further objects, features and advantages of the present invention will be more fully understood by reference to the following detailed description of the presently perferred, but nonetheless illustrative embodiment in accordance with the present invention, when taken in conjunction with the accompanying drawings, wherein:

FIG. 1 is a top plan view of a representative sterilizing tray and instrument sterilizing pin of the present invention, illustrating the arrangement and utilization of the pins to position and hold various surgical instruments.

FIG. 2 is a sectional view, taken substantially along the line 2—2 in FIG. 1 and looking in the direction of the arrows, illustrating the stacking of the surgical instruments on the pins positioned within the sterilizing tray;

FIG. 3 is a front elevational view of the instrument sterilizing pin, showing the space between the straight segments of the pin relative to the spacing between holes in the bottom surface of the sterilizing tray;

FIG. 4 is a side elevational view of the pin;

FIG. 5 is a side elevational view showing the instrument sterilizing pin inserted in the bottom surface of the sterilizing tray; and FIG. 6 is a fragmentary plan view of the sterilizing pin engaged in a segment of the perforated metal in the bottom surface of the sterilizing tray.

Referring now specifically to the drawings and in particular to FIG. 1, there is shown an illustrative instrument sterilizing tray, generally designated by the reference numeral 10, containing a plurality of surgical instrument pins 12 of the present invention. These pins 12 are shown holding stacks of conventional ring-handled clamps 14, scissors 16 and conventional scalpels 18. A tray 10 of the type shown in FIG. 1 is loaded with such surgical instruments and placed in the sterilizing unit. The pins 12 are oriented in the trays 10 relative to each other such that ring-handled movable instruments are held in their open positions for maximum exposure of box locks 20 and ratchets 22 during sterilization. Further, multiple pins 12 can be oriented relative to each other to surround instruments that do not contain ring handles as shown by the pins 12 around the scalpels 18 in FIG. 1.

FIG. 2 shows how pins 12 may be utilized to stack multiple instruments of the same general type obviating the need to sort the instruments after sterilization.

The instrument sterilizing pin in this illustrative form of the invention is comprised of segments 26 connected by an arcuate segment 28 thereby forming a U-shaped member as shown in FIG. 3. The end of each straight segment 26, forms an engaging segment 30, dimensioned to be insertable into holes 32 in the perforated metal bottom surface 34 of the sterilizing tray 10. Typically, such perforations are of ⅛ inch diameter.

A stop 36 is formed on the straight segment 26. Advantageously, the stop 36 is formed by stamping the material in the straight segment 26 so that lateral ears 38 are created as shown in FIG. 4. The ears 38 make the effective diameter of the stop 36 greater than the diameter of the holes 32 in the perforated metal bottom surface 34.

As shown in FIG. 5 the engaging portion 30 of the straight segment 36 is insertable within the holes 32 and slides downward until the ears 38 seat against the top face of the bottom surface 34 of the sterilizing tray 10.

In this illustrative form of the invention, the sterilizing pin 12 is adapted to engage every fourth hole in the perforated metal bottom surface 34 of the sterilizing tray 10, a fragment of which is shown in FIG. 6.

To assure that the sterilizing pin 12 stays in position in the bottom surface 34 of the sterilizing tray 10, the straight segments 26 diverge slightly. As shown in FIG. 3, the space between engaging portions 30 is slightly greater than the space between every fourth hole 32 in the bottom surface 34, requiring the slight compression of the straight segments 26 during engagement with the holes 32. The bottommost end 40 of the engaging portion 30 is spherically shaped to facilitate insertion of the sterilizing pin 12 into the bottom surface 34 of the sterilizing tray 10.

The sterilizing pin 12 is preferably fabricated from corrosion-resistant material, typically stainless steel, to insure that the sterilizing clip will not deteriorate as a result of repeated sterilizing cycles.

As best shown in FIG. 1, the pins can be arranged relative to each other to position surgical instruments of the type without ring handles within the tray during sterilization.

The pins of this invention are high enough to allow similar instruments to be stacked one on top of the other as shown in FIG. 2. Thus, after sterilization there is no need to separate such instruments, reducing the handling of sterile instruments.

From the foregoing, it will be appreciated that there has been provided in accordance with the present invention an improved instrument sterilizing pin and tray combination that can be placed anywhere on the bottom surface 34 of an instrument sterilizing tray 10 in such manner that surgical instruments are held in the most advantageous position for maximum sterilization. Further, a multiplicity of similar instruments can be held in position during sterilization obviating the need for sorting and unnecessary handling of these instruments subsequent to the sterilization operation. Further, surgical instruments such as scalpels, which do not have ring handles are equally well held in position during the sterilizing cycle and the handling of the loaded instrument sterilizing trays incident thereto.

A latitude of modification, change and substitution is intended in the foregoing disclosure. Accordingly, it is appropriate that the appended claims be construed broadly and in a manner consistent with the spirit and scope of the invention.

What is claimed is:

1. An apparatus for sterilizing surgical instruments comprising a sterilizing tray of the type containing a bottom surface of perforated metal and a plurality of instrument sterilizing pins engaged in said bottom surface wherein each instrument sterilizing pin is comprised of a body portion having a pair of substantially parallel straight segments connected by an intermediate segment having a bend occupying a plane formed by said straight segments, each of said straight segments including a stop means consisting of a widened portion of said straight segment and an engaging segment in coaxial alignment with said straight segment, said engaging segments are engagable in perforations in said bottom surface of said sterilizing tray in perforations spaced from each other such a distance that when said engaging segments are engaged in said bottom surface of said tray said sterilizing pins are maintained in a resiliently deflected state with the deflection of said body portion causing said engaging segments to apply a retention force on the sides of the perforations in said bottom surface of said sterilizing tray, said widened portion comprising a lateral ear extending from said substantially straight segment adjacent said engaging segment whereby the effective diameter of said stop means is greater than the diameter of said perforation in said bottom surface of said sterilizing tray.

* * * * *